United States Patent
Filkoski, Jr.

(10) Patent No.: US 10,625,040 B2
(45) Date of Patent: Apr. 21, 2020

(54) HUMIDIFIER FOR CONTINUOUS POSITIVE AIRWAY PRESSURE DEVICE

(71) Applicant: Lawrence Filkoski, Jr., King George, VA (US)

(72) Inventor: Lawrence Filkoski, Jr., King George, VA (US)

(*) Notice: Subject to any disclaimer, the term of this patent is extended or adjusted under 35 U.S.C. 154(b) by 316 days.

(21) Appl. No.: 15/732,203

(22) Filed: Oct. 4, 2017

(65) Prior Publication Data
US 2019/0099580 A1    Apr. 4, 2019

(51) Int. Cl.
*A61M 16/14*    (2006.01)
*A61M 16/10*    (2006.01)
(Continued)

(52) U.S. Cl.
CPC ...... *A61M 16/145* (2014.02); *A61M 16/0875* (2013.01); *A61M 16/107* (2014.02); *A61M 16/16* (2013.01); *A61M 16/109* (2014.02); *A61M 16/1055* (2013.01); *A61M 2205/0205* (2013.01); *A61M 2205/21* (2013.01);
(Continued)

(58) Field of Classification Search
CPC .............. A61M 16/00; A61M 16/0057; A61M 16/0066; A61M 16/0875; A61M 16/1055; A61M 16/107; A61M 16/1075; A61M 16/109; A61M 16/14; A61M 16/16; A61M 2205/0205; A61M 2205/21; A61M 2205/42; A61M 2205/7518; A61M 2205/7545; F24F 6/00; F24F 6/04; F24F 6/043; F24F 2006/008
See application file for complete search history.

(56) References Cited

U.S. PATENT DOCUMENTS

2003/0067086 A1*  4/2003  Mulvaney ............... F24F 6/00
                                                                    261/107
2015/0306324 A1* 10/2015  Ayon ................... A61M 16/06
                                                                    128/204.21
(Continued)

FOREIGN PATENT DOCUMENTS

EP             1619451 A1 *  1/2006  ............ F24F 6/043

*Primary Examiner* — Joseph D. Boecker
(74) *Attorney, Agent, or Firm* — Thomas J. Wallen; Attorney at Law, L.L.C.; Eugene H. Eickholt (57) ABSTRACT

A humidifier is combined with a continuous positive airway pressure device. The continuous positive airway pressure is surrounded by a housing; the humidifier comprises a chamber defined by the continuous positive airway pressure device housing and a wall between the chamber and the continuous positive airway pressure device. The chamber includes a removable air-tight lid, wherein the chamber is filled with a mass transfer medium capable of reversibly absorbing water and wherein air can pass through the mass transfer medium and water is dissolved into the passing air. The chamber can be integrally connected within the continuous positive airway pressure device housing further including a first hose adapter to connect the chamber to an air outlet of a continuous positive airway pressure device whereby air passes from the continuous positive airway pressure device through the chamber and mass transfer medium, thereby humidifying the air, and wherein the humidified air passes through the second hose adapter towards a patient.

6 Claims, 7 Drawing Sheets

(51) Int. Cl.
*A61M 16/16* (2006.01)
*A61M 16/08* (2006.01)
(52) U.S. Cl.
CPC . *A61M 2205/42* (2013.01); *A61M 2205/7518* (2013.01); *A61M 2205/7545* (2013.01)

(56) References Cited

U.S. PATENT DOCUMENTS

| | | | |
|---|---|---|---|
| 2016/0022954 A1* | 1/2016 | Bath | A61M 16/16 128/203.27 |
| 2016/0199605 A1* | 7/2016 | Hamilton | A61M 16/16 128/203.26 |
| 2017/0000968 A1* | 1/2017 | Harrington | A61M 16/109 |
| 2017/0216552 A1* | 8/2017 | Goff | A61M 16/0816 |
| 2017/0319811 A1* | 11/2017 | Foote | A61M 16/0066 |
| 2018/0110944 A1* | 4/2018 | Dai | A61M 16/022 |
| 2018/0333556 A1* | 11/2018 | Ormrod | A61M 16/16 |

* cited by examiner

HUMIDIFIER FOR CONTINUOUS POSITIVE AIRWAY PRESSURE DEVICE

CROSS REFERENCE TO RELATED APPLICATIONS

This application is based on Provisional U.S. Application No. 62/519,167 filed Jun. 13, 2017, and claims benefit therefrom under 35 U.S.C. § 119(e).

STATEMENT REGARDING FEDERALLY SPONSORED RESEARCH OR DEVELOPMENT

Not Applicable

THE NAMES OF PARTIES TO A JOINT RESEARCH AGREEMENT

None

INCORPORATION-BY-REFERENCE OF MATERIAL SUBMITTED ON A COMPACT DISK

None

BACKGROUND OF THE INVENTION

CPAP machine (Continuous Positive Airway Pressure Device) users often struggle with dryness and discomfort in the morning. Therefore, most users also use a humidifier with their machine. Unfortunately, such machines and their humidifiers are large, cumbersome, and not conducive for travel. They also require distilled water, which isn't convenient when sleeping away from home. Further, they require electricity, which means while running on battery power which draws large amounts of electrical current, standard humidifiers cannot be used. Some users may purchase a portable CPAP machine or use a standard CPAP device without the humidifier for traveling. However portable humidifiers are not currently available on the market. An efficient alternative that can be used at home, for travel, or on battery power is needed.

BRIEF SUMMARY OF THE INVENTION

A small portable humidifier that can be attached to any conventional CPAP is disclosed. The humidifier adds moisture to the air expelled from a CPAP therapy device. As designed, it is small in size and does not require electricity, making it ideal for travelers or those in need of backup humidification for their sleep apnea therapy devices. This prevents dryness and discomfort that may occur when they are not able to utilize a larger machine and humidifier or while using battery run devices. This device makes it easier to travel with a CPAP device without giving up the added comfort of humidification. It aids in further filtering the air flow, extracting undesirable particles from the air. The device also reduces CPAP noise as it dampens the sounds from the CPAP device motor. The present invention can be used with regular bottled or distilled water.

A CPAP Humidifier helps CPAP users comfortably sleep at night without the hassle of large, bulky equipment. The invention comprises a portable humidifier for sleep apnea devices, such as CPAP machines or BiLevel machines. The humidifier is small, lightweight, and designed for ease of travel and portability. It may be collapsible or expandable in order to minimize its size when traveling. The humidifier may be attached or be integrated directly with a CPAP unit. The device can include a rectangular, enclosed chamber, approximately 5" in length, 2" in width, and 3" in height. The device will contain an insert made of a disposable or reusable wicking material, such as paper, sponge, or other absorbent material with shaped cells that are air permeable, so that the airflow from a CPAP machine can freely pass through from one end of the chamber to the other end. In use, water is added to the chamber and the absorbent insert becomes saturated with water. Distilled water or bottled water is adequate. As air is circulated by the CPAP machine through the chamber it is exposed to the many channels or passages of the insert and the exiting air is greatly humidified. Additionally, either end of the humidifier can have openings with adapters to secure both a CPAP device on one and a hose that leads to the user on the other.

In another embodiment of the invention an antimicrobial agent can be added to the absorbent insert. This eliminates or reduces harmful growth on the mass transfer medium.

DETAILED DESCRIPTION OF THE INVENTION

The present invention helps CPAP users comfortably sleep at night without the hassle of large, bulky equipment. The device comprises a portable humidifier for sleep apnea devices, such as CPAP machines. The humidifier is small, lightweight, and designed for ease of travel and portability. It may be collapsible or expandable in order to minimize its size when traveling. The humidifier may be attached or be integrated directly with a CPAP unit. In a preferred embodiment, the device can include a rectangular, enclosed chamber, approximately 5" in length, 2" in width, and 3" in height. The device will contain an insert made of a disposable or reusable wicking material, such as paper, sponge, or other absorbent material with shaped cells that are air permeable, so that the airflow from a CPAP machine can freely pass through from one end of the chamber to the other end. In use, water is added to the chamber and the absorbent insert becomes saturated with water. As air is circulated by the CPAP machine through the chamber it is exposed to the many channels or passages of the insert and the exiting air is greatly humidified. Additionally, either end of the humidifier can have openings with adapters to secure both a CPAP device on one and a hose that leads to the user on the other. The humidifier may contain a one-way valve or other adaptation to prevent water from flowing back into the CPAP device.

The insert made of wicking absorbent material is the primary part of the humidifier that accomplishes the solutions as provided. This insert can be made to fit any existing CPAP humidifier if the design allows for it. In addition to providing moisture, the insert can also act as a filter or purifier by extracting unwanted particles from the air that circulates through it. This insert can also dampen or reduce noise coming from the CPAP device, further enhancing the therapy. The humidifier may be integrated with a heating source such as a heating element, heating plate, or other heating design to further enhance its effectiveness. The exact specifications may vary upon manufacturing.

Figure 1:
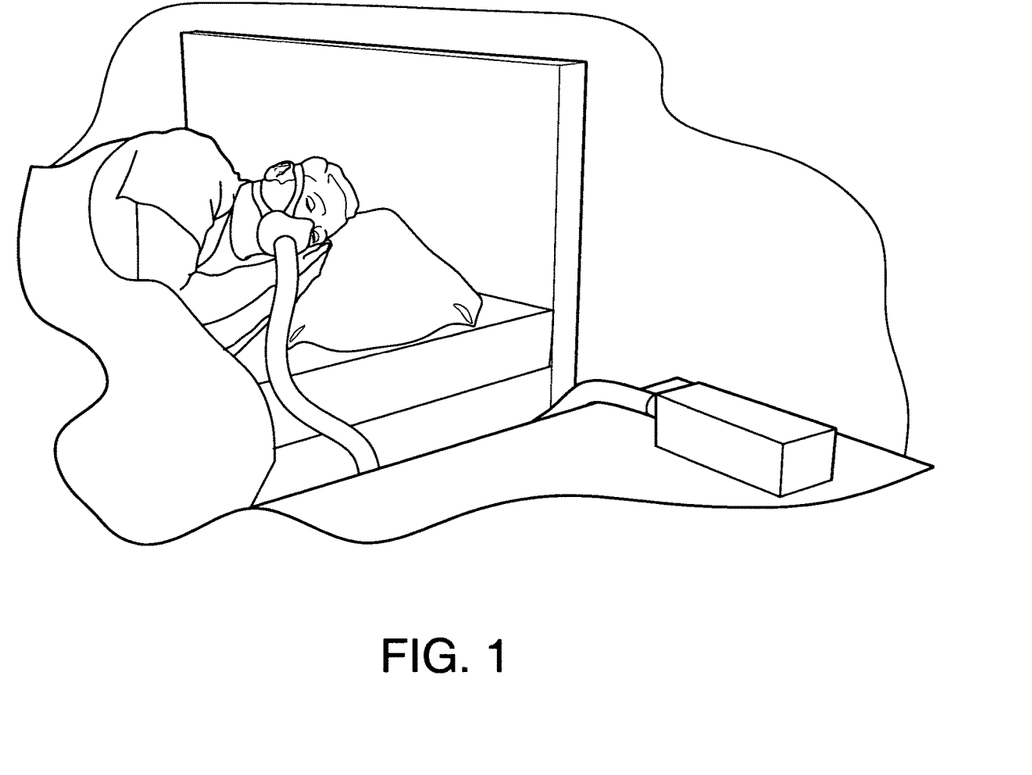
FIG. 1 shows a man sleeping with the humidifier attached to his CPAP machine.

FIG. 1 shows a conventional CPAP machine as it appears in use. The CPAP machine rests on a table or other convenient surface and is connected to a mask worn by a user while the user sleeps.

Figure 2:
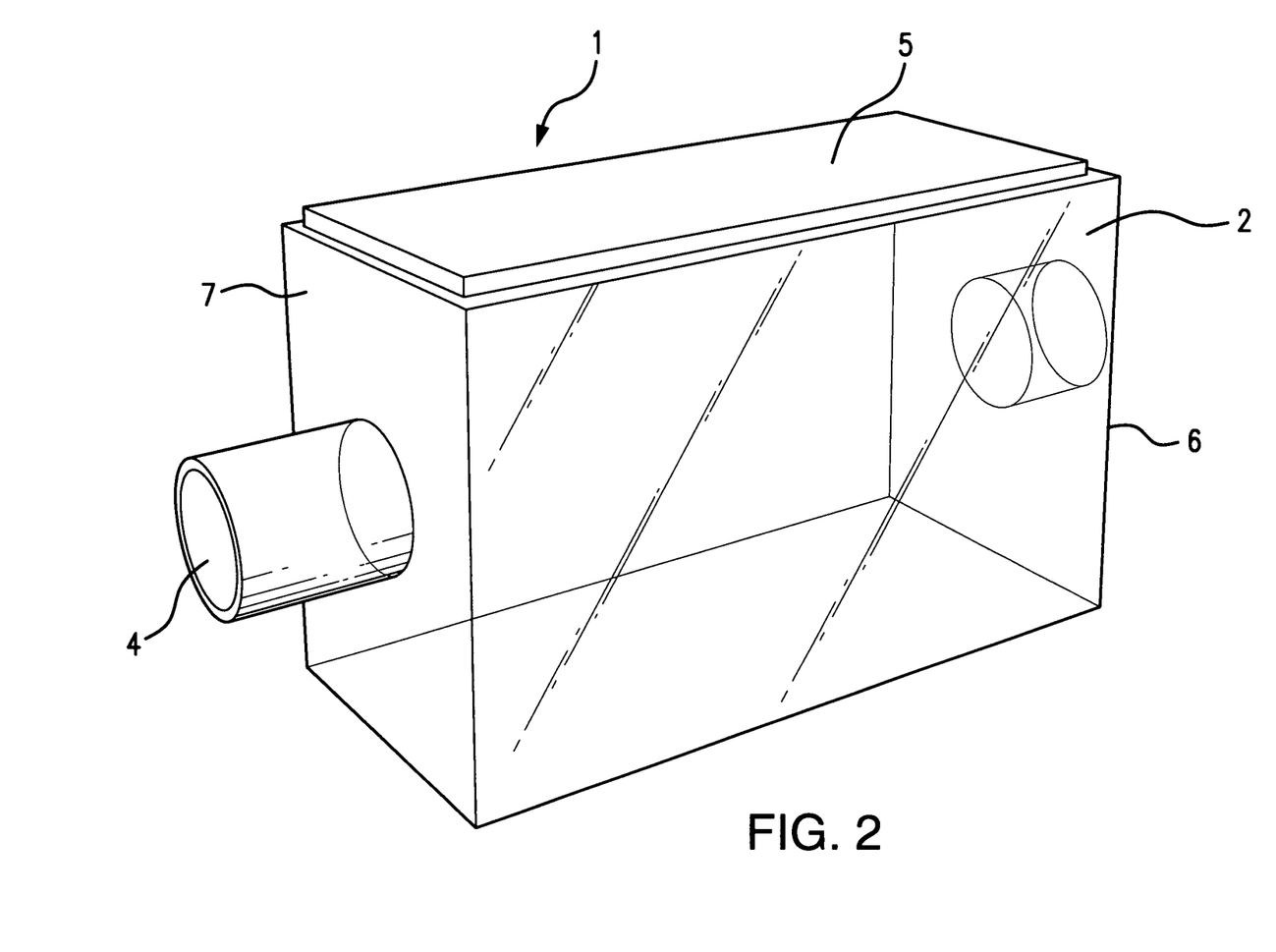
FIG. 2 shows the humidifier according to the invention
Figure 3:
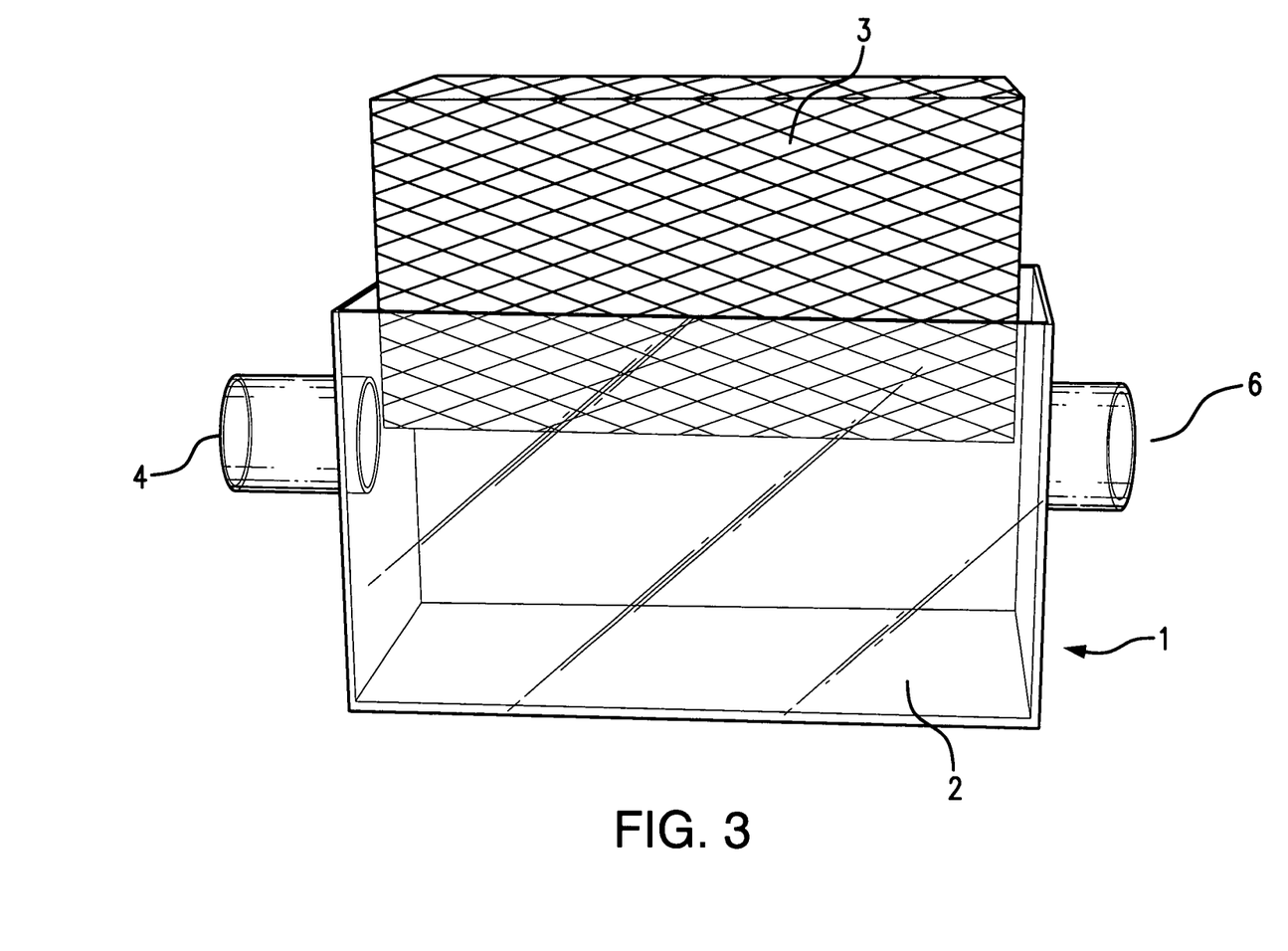
FIG. 3 shows the humidifier chamber with the lid removed and a mass transfer medium partially installed in the mass transfer chamber.

Referring to FIG. 2 the humidifier (1) according to the invention comprises a chamber (2) including a mass transfer medium (3), seen in FIG. 3, through which dry atmospheric air passes. The atmospheric air is humidified as it passes by or through the mass transfer medium (3), ensuring that air with appropriate percentages of water is delivered to the patient to aid in respiration. In the preferred embodiment, the mass transfer medium (3) comprises a wicking material that readily absorbs or adsorbs water and delivers the water to a passing stream of air. Suitable wicking materials include paper, especially paper with shaped cells. Hydrogels that reversibly absorb water are also usable in the invention. Although paper and hydrogels are typically usable, it is expressly understood that the invention is not limited to any particular mass transfer medium. The mass transfer material can be either disposable or reusable. The important criteria is the mass transfer medium be air flow permeable, such as air flow permeable paper.

Chamber (2) can be any shape that provides adequate contact between passing air and the mass transfer medium (3). The larger the surface area of mass transfer medium (3) that is exposed to the passing air, the more water that will be absorbed by the passing air stream, up to the point where the air stream becomes saturated. Therefor the upper limit on the surface area of the mass transfer medium is determined by the volume of air to be treated per unit time. Although a rectangular shaped chamber is illustrated, any shaped chamber could be equally used. A lid (5) is provided, which lid could be completely removable or hinged to chamber (2). The lid of FIG. 2 and FIG. 3 is completely removable by separating the lid (5) from chamber (2) along the top periphery of chamber (2). It expressly understood that any peripheral closure between lid (5) and chamber (2) is suitable, with or without hinges. The important consideration is that the closure between lid (5) and chamber (2) be sufficiently air-tight to prevent air from passing between lid (5) and chamber (2) thereby bypassing mass transfer medium (3).

FIG. 3 shows the humidifier with lid (5) removed from chamber (2). Mass transfer medium (3) is half-way inserted into chamber (2). A honeycombed or air flow permeable paper mass transfer medium is depicted for mass transfer medium (3). In use the medium (3) is completely inserted into chamber (2), then saturated with liquid water. After saturation of medium (3), lid (5) is attached in an air-tight manner to prevent air from short circuiting and passing around mass transfer medium (3). It has been found best to completely fill chamber (2) with mass transfer medium (3) to prevent channeling between the inside walls of chamber (2) and mass transfer medium (3). If excessive channeling occurs, insufficient humidification results. Indent (7), seen in FIG. 2, is provided on each side of chamber (2) to aid in removal of lid (5). In practice, the user can place his fingers in indents (7) below the bottom periphery of lid (5), and push lid (5) up and separate lid (5) from chamber (2). The unit can be designed with or without a removable lid. A unit intended to be disposable may not require a lid as it can be filled with water through the air outlet or inlet. A unit intended to be reusable may have a lid or opening to allow replacement of the insert.

Referring to FIG. 2 and FIG. 3, a hose adapter is provided at both ends of humidifier (1). Hose adapter (4) is designed to connect a hose to the patient, while hose adapter (6) connects to the CPAP machine. Air passes from the CPAP machine through chamber (2) and out to the patient. When the air passes through chamber (2) water humidifies the air by diffusion into the air because the air is below saturation. The diffusion process proceeds by evaporation with forced convection as the air stream is forced through mass transfer medium (3). The available surface area necessary to adequately humidify the air stream varies according to the mass transfer medium. Of course the air stream is within the range of normal human respiration, so the mass transfer medium is selected to properly humidify that range of volumetric flow rate. In the preferred embodiment the mass transfer medium will saturate the normal volumetric flow rate of air for at least eight-hours, or through the night for a user that is sleeping. The humidifier may contain a one-way valve or other adaptation to prevent water from flowing back into the CPAP device.

Figure 4:
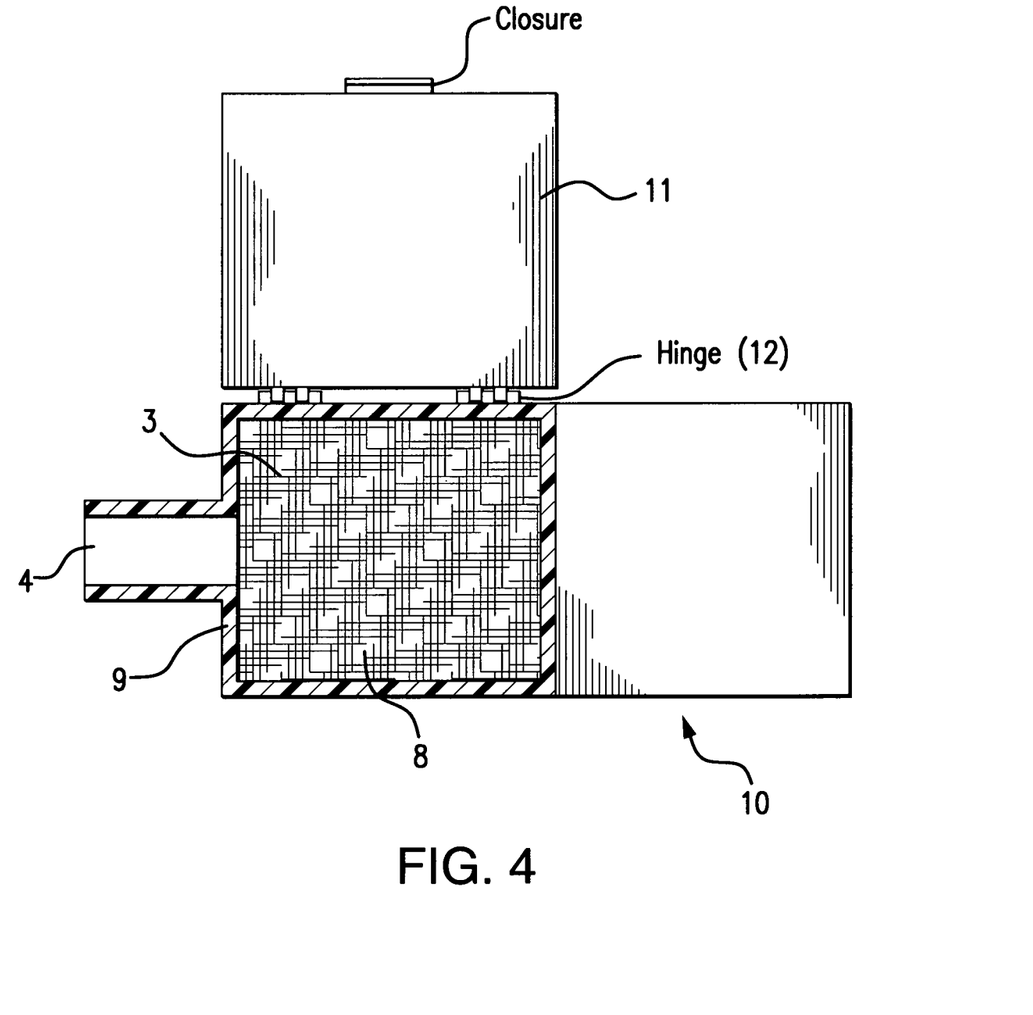
FIG. 4 shows an integral humidifier and CPAP machine.

In an alternate embodiment of the invention, as seen in FIG. 4, the humidifier is an integral component of a CPAP machine. In this embodiment the humidifier chamber (8) is located within the housing (9) of the CPAP machine (10). Mass transfer medium (3) is located in chamber (8). Lid (11) removably covers the CPAP housing (9) to allow the user to clean the chamber (8), change the mass transfer medium, and add water. This embodiment is preferred for a new CPAP machine, while the add-on humidifier is useful with CPAP machines that do not currently have humidification. Hinges (12) connect lid (11) to housing (9); however it is expressly understood that any peripheral closure between lid (11) and housing (9) is suitable, with or without hinges (12). The important consideration is that the closure between lid (11) and housing (9) be sufficiently air-tight to prevent air from passing between lid (11) and housing (9) thereby bypassing mass transfer medium (3).

Figure 5:
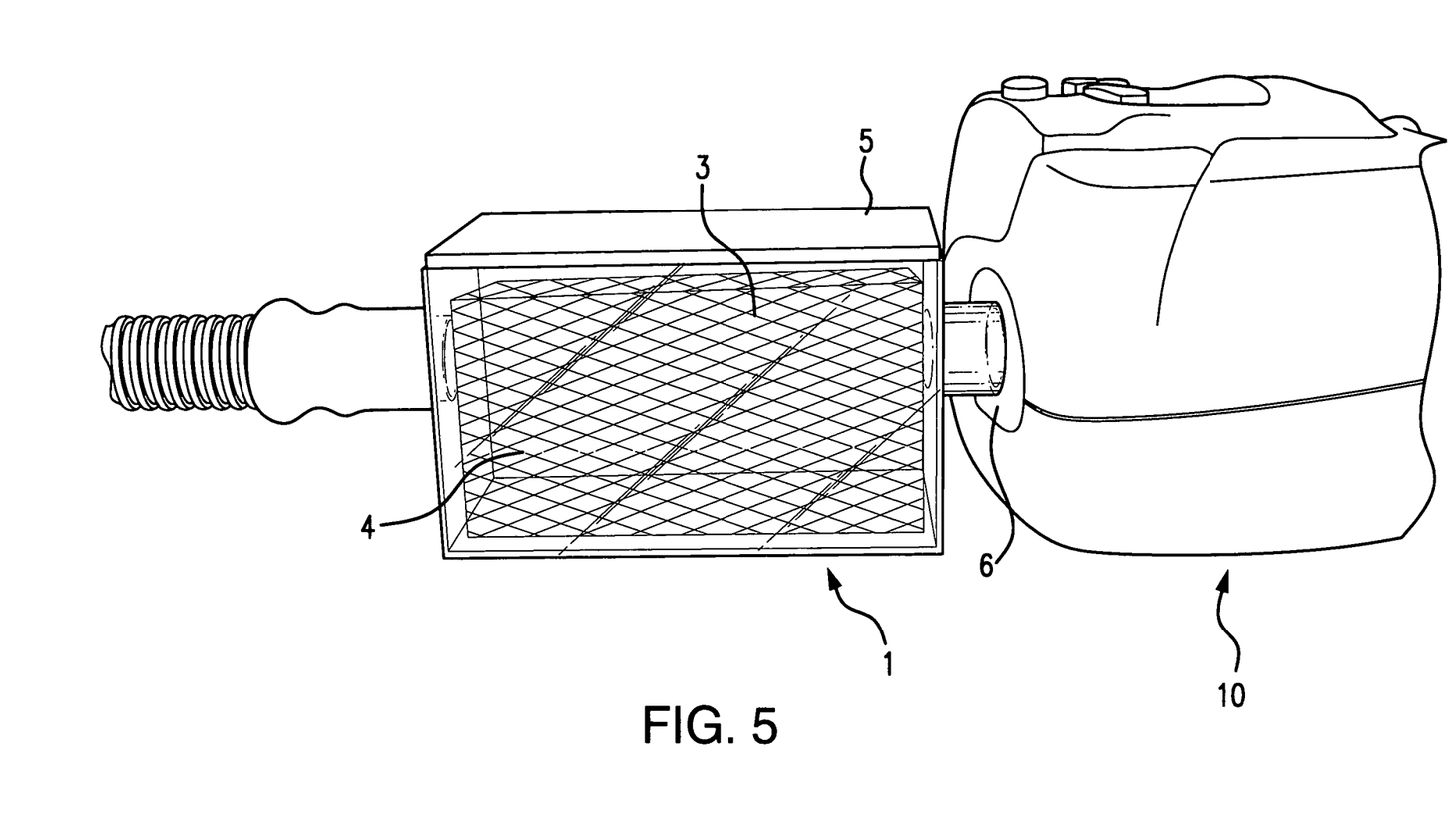
FIG. 5 shows the humidifier connected to a CPAP machine ready to attach to a patient.

FIG. 5 shows the humidifier (1) connected to CPAP machine (10).

An alternate embodiment of the instant invention includes a flow diverting lid to minimize ware flowing back into the CPAP machine. A flow diverting lid is used in combination with a continuous positive airway pressure device. The lid comprises a horizontal bottom wall and a parallel horizontal top wall, and four vertical sides forming a rectangular shaped chamber adapted to fit atop a humidifier chamber. Further an interior divider wall is an integral part of the lid wherein the interior divider wall is secured perpendicularly to and interposed between the horizontal bottom wall and the horizontal top wall, thereby forming a forward dry air pathway and a reverse dry air pathway. The forward and reverse dry air pathways are formed between the top and bottom horizontal walls, wherein dry air from the continuous positive airway pressure device enters the humidifier chamber through an inlet where it is diverted toward the user along the interior divider wall along the forward dry air pathway. The dry air then turns 180 degrees and flows back towards the continuous positive airway pressure device inlet along the reverse dry air pathway To prevent the forward dry air pathway from mixing with the reverse dry air pathway, a first dry air pathway from the humidifier chamber inlet to the forward dry air pathway is provided, and a second dry air pathway flowing from the reverse dry air pathway and into the humidifier chamber is also provided. The first and second dry air pathways could be any suitable arrangement of interior walls or tubes.

Figure 6:
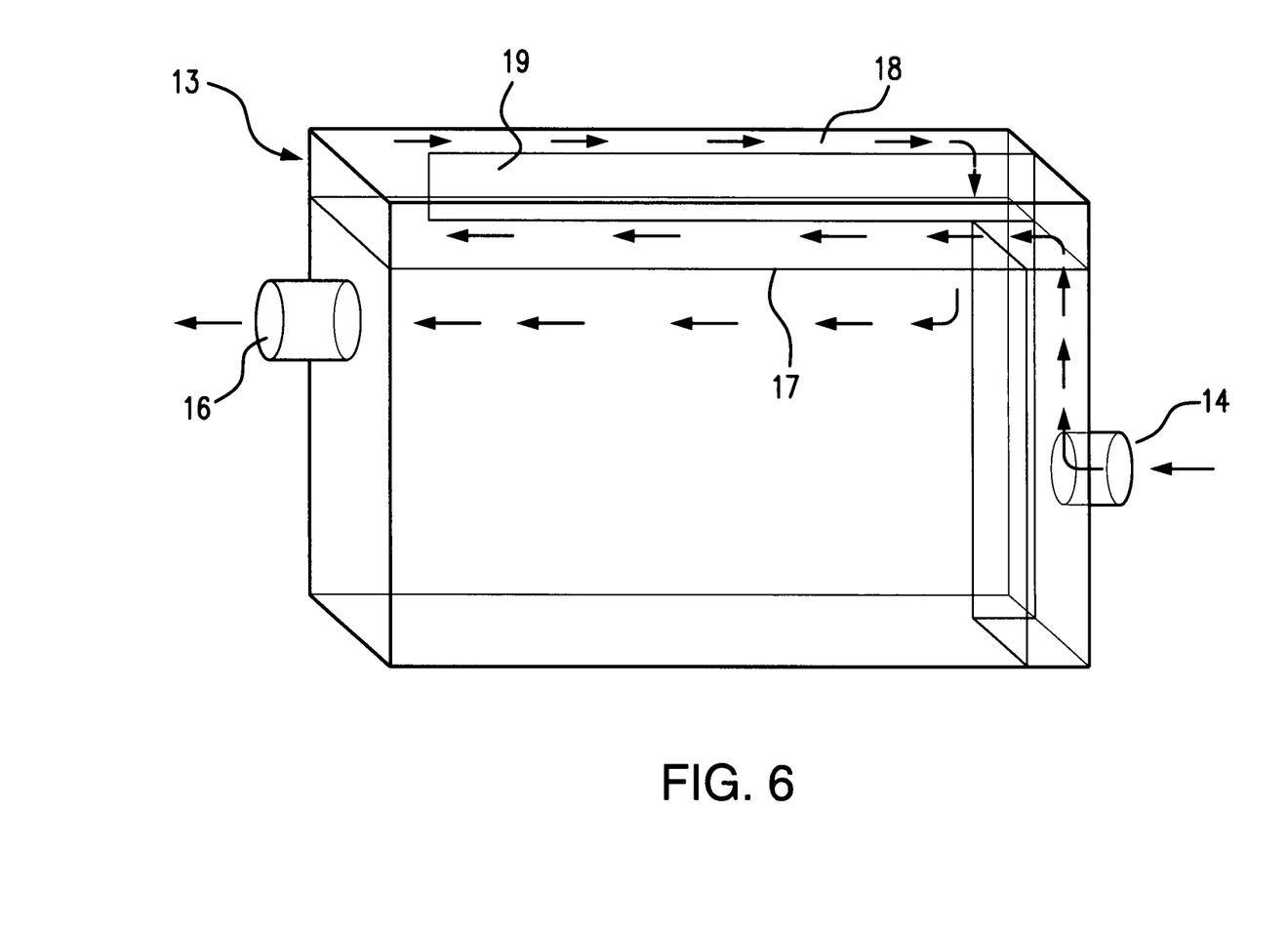
FIG. 6 shows an alternate embodiment of the CPAP humidifier that includes a flow diverting lid.

FIG. 6 shows details of the alternate embodiment of the instant humidifier that includes a flow diverting lid (13) to minimize water circulation into the CPAP machine. In the event that the unit falls down accidently from its position during use water cannot travel back into the machine and cause damage. A one-way valve interposed between the CPAP machine and the humidifier could also accomplish this result, or be used in combination with the flow diverting lid (13).

Figure 7A:
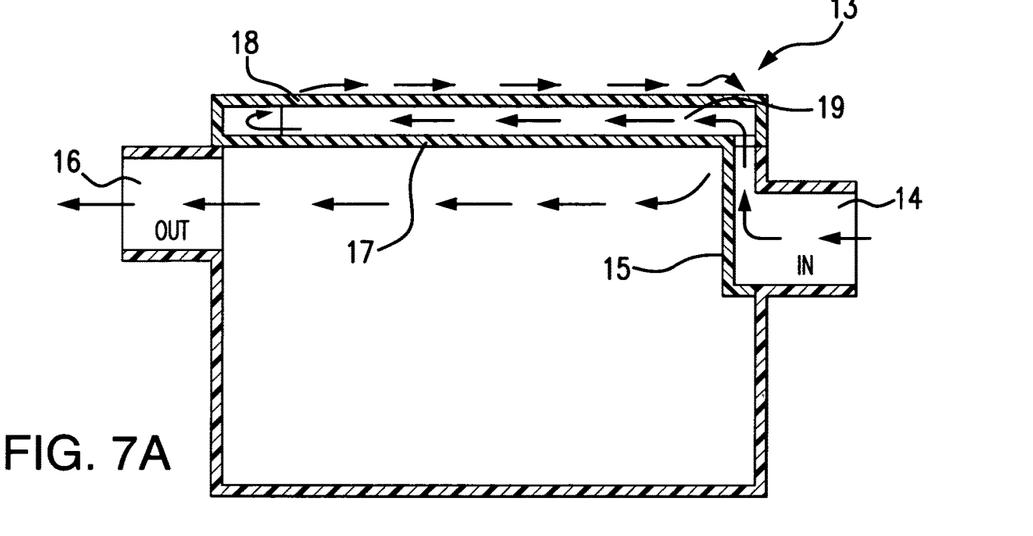
FIG. 7A shows the CPAP humidifier of FIG. 6 in horizontal side view.
Figure 7B:
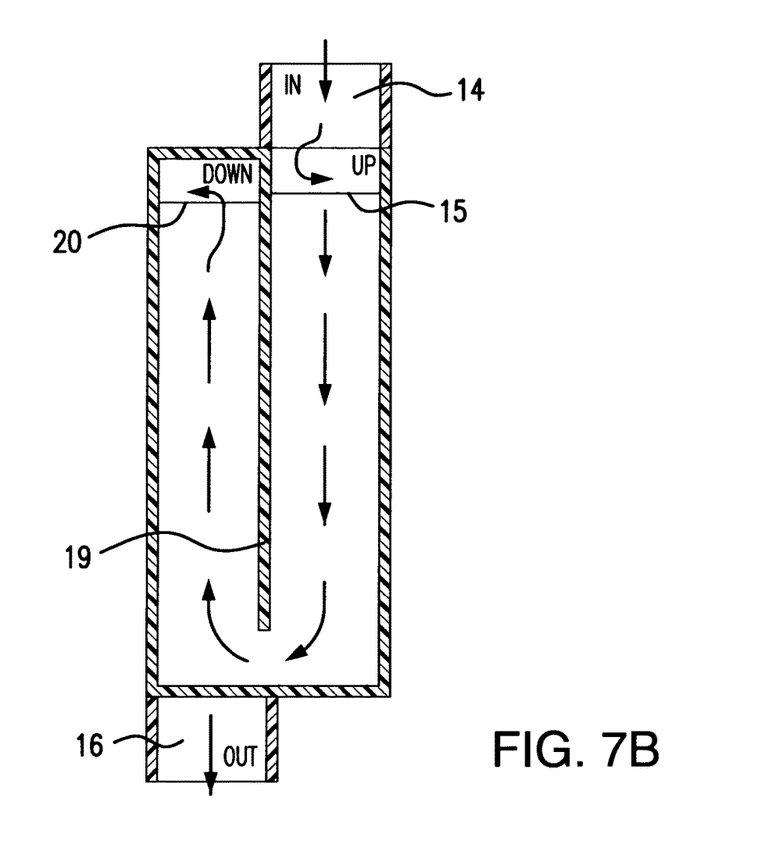
FIG. 7B shows the CPAP humidifier of FIG. 6 in profile end view.

FIG. 7 shows details of the flow diverting lid (13) seen in FIG. 6. Lid (13) comprises horizontal bottom wall (17) and parallel horizontal top wall (18), and four vertical sides forming a rectangular shaped chamber that fits atop humidifier chamber (2). Vertical wall (19) which is an integral part of lid (13), is secured perpendicularly to and between horizontal walls (17) and (18). Air from the CPAP machine enters through hose adapter or inlet orifice (14) where it is diverted 90 degrees up along wall (15). The lower portion of orifice (14) that faces the bottom of chamber (2) intersects vertical wall (15) such that dry air must turn 90 degrees and flow upward towards lid (13). Vertical wall (15) wall is parallel to the outside vertical side wall of chamber (2) that faces the CPAP machine through which orifice (14) communicates to the CPAP machine. In this way dry air that enters the humidifier through orifice (14) must pass vertically to the lid (13). Dry air then turns 90 degrees and passes between vertical wall (19) and the outside vertical wall of lid (13). Wall (19) does not extend completely to the vertical side wall of lid (13) that faces the user providing a path for dry air to turn 180 degrees and return to the inlet side of the humidifier chamber (2). In this way air delivered through orifice (14) passes along wall (15) then between wall (17) and the upper surface (18) of lid (13), then returns to the inlet side of humidifier chamber (2). Another wall structure (20) provides a vertical path to return dry air downwards to the CPAP inlet side of the humidifier so the dry air can then pass through the mass transfer medium. Opening (20) communicates with the inlet orifice side of the mass transfer medium before flowing through the medium and exiting to the user. Dry air then passes through mass transfer medium (3) in humidifier chamber (2) and exits towards the user.

It is contemplated that an antimicrobial agent can be added to the absorbent insert. It is important that the antimicrobial agent is bound to the mass transfer medium and is not releasable into the air, because the antimicrobial agent could potentially kill beneficial microbial flora in the patient. With this embodiment the air delivered to the patient is not only humidified, but also treated to kill common microbial organisms.

The present invention affords many advantages over current CPAP machines. Portability greatly aids the user when traveling. Because the design is simple and economical, the user can dispose the device should they so choose, or alternatively easily clean and reuse the device almost indefinitely. The unit can be designed with or without a removable lid. A unit intended to be disposable may not require a lid as it can be filled with water through the air outlet or inlet. A unit intended to be reusable may have a lid or opening to allow replacement of the insert. An additional advantage is the humidifier aids in further purifying the air that passes from the CPAP or Bi-Level device.

The humidifier requires no electricity, however the humidifier can be integrated with a heating source such as a heating element, heated wire, heating plate, or other type of heat generating technology to further enhance humidification delivery.

The invention claimed is:

1. A humidifier combined with a continuous positive airway pressure device the continuous positive airway pressure device and humidifier surrounded by a housing, the humidifier comprising a chamber defined by the housing and a wall between the chamber and the continuous positive airway pressure device, including a removable air-tight lid, the chamber being completely filled with a mass transfer medium capable of reversibly absorbing water, wherein a majority of air from the continuous positive airway pressure device can pass through the mass transfer medium and wherein water is dissolved into the passing air, wherein the chamber is integrally connected within the housing further including a first hose adapter to connect the chamber to an air outlet of the chamber whereby air passes from the continuous positive airway pressure device through the chamber and mass transfer medium, thereby humidifying the air, and wherein the humidified air passes through the first hose adapter towards a user.

2. The humidifier of claim 1 wherein the mass transfer medium is air flow permeable paper.

3. The humidifier of claim 1 wherein the mass transfer medium is a hydrogel.

4. The humidifier of claim 1 wherein the mass transfer medium further includes an antimicrobial bound to the mass transfer medium that is not releasable into the air.

5. The humidifier of claim 1 wherein the mass transfer medium filters the air as it passes the chamber.

6. The humidifier of claim 1 wherein the humidifier dampens noise levels created by the continuous positive airway pressure device.

* * * * *